United States Patent [19]
Wolf, Jr. et al.

[11] Patent Number: 5,868,695
[45] Date of Patent: Feb. 9, 1999

[54] SYSTEMS AND METHODS FOR ERADICATING CONTAMINANTS USING PHOTOACTIVE MATERIALS IN FLUIDS LIKE BLOOD USING DISCRETE SOURCES OF RADIATION

[75] Inventors: Ludwig Wolf, Jr., Inverness; John T. Foley, Wheeling; William R. Bratten, Lake Villa, all of Ill.; Gary Kunz; Michael Stonefield, both of Vancouver, Canada

[73] Assignees: Baxter International Inc., Deerfield, Ill.; Quadra Logic Technologies Inc., Vancouver, Canada

[21] Appl. No.: 174,211

[22] Filed: Dec. 28, 1993

(Under 37 CFR 1.47)

Related U.S. Application Data

[63] Continuation of Ser. No. 945,855, Sep. 16, 1992, abandoned, which is a continuation of Ser. No. 630,838, Dec. 20, 1990, abandoned.

[51] Int. Cl.$^6$ ..................................................... A61M 1/00
[52] U.S. Cl. ................................... 604/4; 604/20; 604/28
[58] Field of Search .................................. 604/4, 5, 6, 19, 604/20, 21, 27, 28; 424/529; 514/908; 606/1, 3, 18; 607/88

[56] References Cited

U.S. PATENT DOCUMENTS

| | | |
|---|---|---|
| 2,308,516 | 1/1943 | Knott . |
| 4,181,128 | 1/1980 | Swartz . |
| 4,321,919 | 3/1982 | Edelson . |
| 4,398,906 | 8/1983 | Edelson . |
| 4,402,318 | 9/1983 | Swartz ......................................... 604/20 |
| 4,428,744 | 1/1984 | Edelson . |
| 4,456,512 | 6/1984 | Bieler et al. ............................. 210/748 |
| 4,573,962 | 3/1986 | Troutner . |
| 4,612,007 | 9/1986 | Edelson . |
| 4,613,322 | 9/1986 | Edelson . |
| 4,683,889 | 8/1987 | Edelson . |
| 4,684,521 | 8/1987 | Edelson . |
| 4,705,498 | 11/1987 | Goss . |
| 4,708,715 | 11/1987 | Troutner et al. . |
| 4,726,949 | 2/1988 | Miripol et al. . |
| 4,727,027 | 2/1988 | Wiesehahn et al. . |
| 4,737,140 | 4/1988 | Lee et al. . |
| 4,769,131 | 9/1988 | Noll et al. ................................. 210/748 |
| 4,775,625 | 10/1988 | Sieber . |
| 4,822,335 | 4/1989 | Kawai et al. . |

(List continued on next page.)

FOREIGN PATENT DOCUMENTS

| | | |
|---|---|---|
| 0 138 489 | 4/1985 | European Pat. Off. . |
| 0 240 149 | 9/1987 | European Pat. Off. . |
| 92903137.5 | 7/1993 | European Pat. Off. . |

OTHER PUBLICATIONS

Matthews et al., "Photodynamic Therapy of Viral Contaminants with Potential for Blood Banking Applications", *Transfusion*, v. 28,1 1988 pp. 81–83.

*Primary Examiner*—Sam Rimell
*Attorney, Agent, or Firm*—Daniel D. Ryan

[57] ABSTRACT

A system and method for treating a fluid carrying a contaminant to which a photoactive material has been bound include a treatment device that defines a flow passage with a gap. The system and method operate to establish a flow of fluid from the inlet end of the gap to the outlet end of the gap. The system and method also channel the flow of fluid in the gap in succession through one or more flow paths. The system and method establish at least two discrete sources of radiation in the flow path at spaced apart locations along the direction of fluid flow. At least one of the radiation sources comprises a photodiode. The system and method further include a control for operating each discrete source of radiation at a selected wavelength within the prescribed range to activate the photoactive material bound to the contaminant. Upon activation, the material eradicates the contaminant. The system and method provide extracorporeal treatment of fluids like blood to quickly and effectively eradicate infection agents at relatively high flow rates.

18 Claims, 6 Drawing Sheets

U.S. PATENT DOCUMENTS

| | | |
|---|---|---|
| 4,831,268 | 5/1989 | Fisch et al. . |
| 4,838,852 | 6/1989 | Edelson et al. .............................. 604/4 |
| 4,878,891 | 11/1989 | Judy et al. . |
| 4,889,129 | 12/1989 | Dougherty et al. . |
| 4,915,638 | 4/1990 | Sieber . |
| 4,921,473 | 5/1990 | Lee et al. . |
| 4,944,883 | 7/1990 | Schoendorfer et al. . |
| 4,950,255 | 8/1990 | Davidner et al. . |
| 4,983,307 | 1/1991 | Nesathurai .............................. 210/748 |
| 5,030,200 | 7/1991 | Judy et al. ................................. 604/5 |
| 5,032,241 | 7/1991 | Robertson et al. ................. 210/748 X |
| 5,069,885 | 12/1991 | Ritchie ............................... 210/748 X |
| 5,078,673 | 1/1992 | Abrams . |

SYSTEMS AND METHODS FOR ERADICATING CONTAMINANTS USING PHOTOACTIVE MATERIALS IN FLUIDS LIKE BLOOD USING DISCRETE SOURCES OF RADIATION

This is a continuation of application Ser. No. 07/945,855 filed on Sep. 16, 1992, now abandoned, which is a continuation of application Ser. No. 07/630,838, filed Dec. 20, 1990 (now abandoned).

FIELD OF THE INVENTION

The invention generally relates to the eradication of contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immunodeficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components prior to storage and transfusion. See Matthews et al, "Photodynamic Therapy of Viral Contaminants With Potential for Blood Bank Applications," *Transfusion*, 28(1), pp. 81–83 (1988). Various extracorporeal systems have been proposed that use photodynamic therapy to treat blood prior to storage and transfusion. See, for example, Edelson U.S. Pat. Nos. 4,613,322 and 4,684,521; Troutner et al U.S. Pat. No. 4,708,715; Wiesehahn et al U.S. Pat. No. 4,727,027; Sieber U.S. Pat. Nos. 4,775,625 and 4,915,683; and Judy et al U.S. Pat. No. 4,878,891.

To date, there has been a general lack of success in economically adapting the benefits of photodynamic therapy to the demands of the blood banking industry. The extracorporeal systems proposed to date have not been able to provide acceptable levels of eradication at the relatively high flow rates required to economically process therapeutic units of blood components.

For this and other reasons, the promise of photodynamic therapy in treating the nation's banked blood supply has gone largely unfulfilled.

SUMMARY OF THE INVENTION

The inventors have discovered that systems and methods can be provided that accommodate relatively high processing flow rates and yet achieve an acceptably high rate of contaminant eradication through photodynamic therapy. The invention provides extracorporeal systems and methods that quickly and effectively eradicate infectious agents from fluids like blood by flowing the fluids with photoactive material added rapidly past a sequence of discrete radiation sources.

One aspect of the invention provides a system for treating a fluid carrying a contaminant to which a photoactive material has been bound. The system directs fluid through a treatment chamber in a predetermined flow path. The system establishes at least two discrete sources of radiation in the flow path at spaced apart locations along the direction of fluid flow. Each discrete source is a self-contained emitter of radiation that establishes its own zone of radiation. At least one of these discrete radiation sources comprises a photodiode. The system operates each discrete source of radiation at a selected wavelength within the prescribed range to activate the photoactive material bound to the contaminant.

According to another aspect of the invention, the system operates to establish a flow of fluid through the treatment chamber in which the fluid is channelled in succession through at least two different flow paths.

According to this aspect of the invention, the system establishes discrete sources of radiation along both flow paths. The system places at least two of these discrete sources of radiation in the first path at spaced apart locations along the direction of fluid flow. The system also places at least two additional discrete sources of radiation in the second path at spaced apart locations along the direction of fluid flow.

The system further includes a control element for operating each discrete source of radiation at a selected wavelength within a range that activates the photoactive material bound to the contaminant. Upon activation, the material eradicates the contaminant.

By channeling the fluid through several discrete zones of radiation at a relatively high flow rate, the invention provides a surprisingly effective cumulative effect in terms of overall degree of contaminant eradication over a relatively short period of time.

By using discrete sources of radiation, the system also offers the flexibility to meet the needs of differing processing techniques. For example, in one arrangement, the control element operates the discrete sources of radiation at substantially the same wavelength. In another arrangement, the control element operates at least two of the discrete sources of radiation at different wavelengths.

In a preferred embodiment, at least two discrete sources of radiation are positioned along opposite sides of both the first and second flow paths. In this preferred arrangement, there are at least three discrete sources of light positioned along each flow path. Two of the discrete sources are positioned at spaced apart locations along one side of the flow path in the direction of fluid flow, while the other discrete source is positioned on an opposite side of the flow path.

In a preferred embodiment, each discrete source of radiation comprises a photodiode. Each discrete source can thereby be controlled to emit a relatively narrow band of radiation having a relatively precise wavelength. The fluid passes rapidly through these well defined bands of radiation while being treated.

By using photodiodes as sources of radiation, relatively low voltages can be used. The low voltages reduce the amount of heat generated by the system, thereby preserving the viability of the fluid during treatment.

Another aspect of the invention provides a method for treating a fluid carrying a contaminant to which a photoactive material has been bound. According to this aspect of the invention, fluid is conveyed through a gap while being channelled through a predetermined flow path. As it transits the flow path, the fluid is exposed to at least two discrete sources of radiation that are at spaced apart locations along the direction of fluid flow. At least one, and preferably all, of the discrete sources comprises a photodiode.

In another arrangement, fluid is conveyed through a gap while being channelled within the gap in succession through two different flow paths. As it transits the first flow path, the fluid is exposed to at least two discrete sources of radiation that are at spaced apart locations along the direction of fluid flow. As it next transits the second flow path, the fluid is further exposed to at least two additional discrete sources of radiation that are also at spaced apart locations along the direction of fluid flow. Each discrete source of radiation is operated at a selected wavelength within the prescribed range to activate the photoactive material bound to the contaminant as the fluid flows in succession through the two paths.

The systems and methods that embody the features of the invention are applicable for use in environments where sterility and biologically closed system integrity must be maintained during processing. The systems and methods therefore readily lend themselves to blood processing applications.

Other features and advantages of the invention will be pointed out in, or will be apparent from, the drawings, specification and claims that follow.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 1:
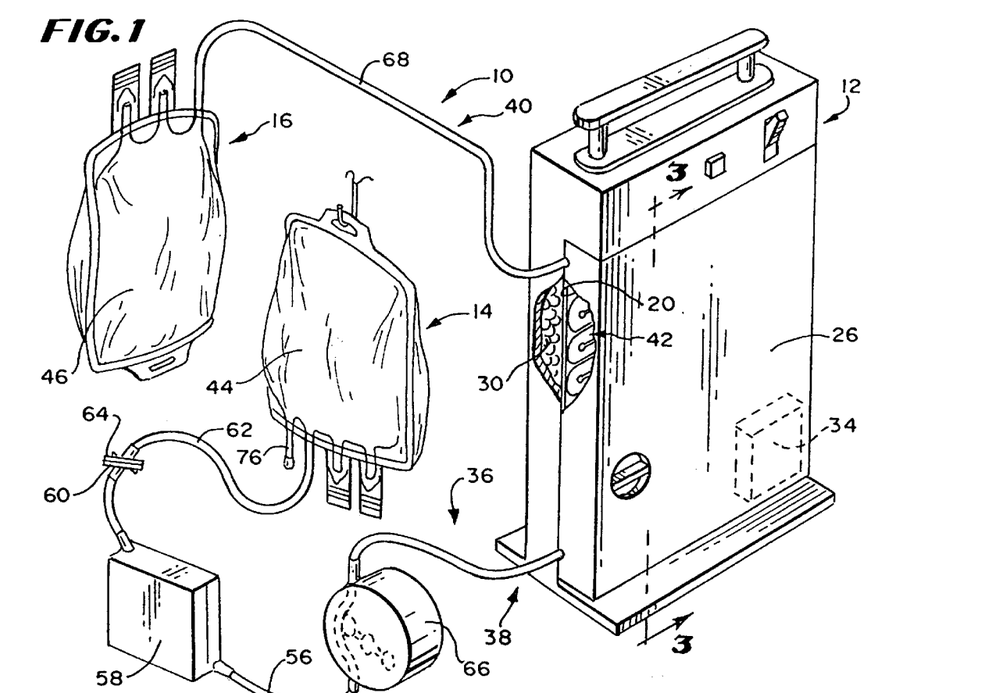
FIG. 1 is a perspective view, with portions broken away, of a system for treating a fluid carrying a contaminant with the treatment chamber closed as it is in use.

FIG. 1 shows a system 10 for treating a fluid carrying a contaminant that embodies the features of the invention. The system 10 includes a treatment device 12 that receives the fluid from a source container 14 and conveys the fluid after treatment to a collection container 16.

The fluid to be treated can vary. In the illustrated embodiment, the fluid comprises a component of whole human blood that is intended to be stored for transfusion. More specifically, the fluid consists of red blood cells suspended in plasma. Typically, a quantity of white blood cells is also present with the red blood cells. The fluid can also include an anticoagulant and, optionally, a storage medium for the blood component. Alternatively, the fluid can consist of platelets suspended in plasma.

In the illustrated embodiment, the contaminant comprises a pathogenic virus typically carried in the blood. For example, the contaminant can consist of the hepatitis-B virus; the human immunodeficiency virus; the Herpes virus; or the influenza virus.

The fluid in the source container 14 includes a photoactive material that has an affinity for the contaminant carried by the fluid. The photoactive material is added to the blood contained in the source container 14 after the blood is collected from a donor. The step of adding the photoactive material will be described in greater detail later.

Due to its affinity for the contaminant, the photoactive material becomes bound to the contaminant within the source container 14. The photoactive material is of a type that becomes active by exposure to radiation within a prescribed wavelength range. When activated by radiation, the material eradicates the contaminant.

Various types of photoactive materials can be used. In the illustrated embodiment, the photoactive compound comprises a family of light-activated drugs derived from benzoporphyrin. These derivatives are commonly referred as BPD's. BPD's are commercially available from Quadra Logic Technologies, Inc., Vancouver B.C., Canada.

BPD's, like other types of hematoporphyrin materials, have an affinity for the cell walls of many viral organisms that are carried in blood. They therefore bind or attach themselves to the biological cell wall of these organisms. When exposed to radiation, BPD's undergo an energy transfer process with oxygen, forming a singlet oxygen. When the singlet oxygen oxidizes, it kills the biological cells to which it has attached. BPD's are described in greater detail in Judy et al U.S. Pat. No. 4,878,891.

According to the invention, the contaminant to which the BPD's is attached is exposed to the radiation in a predetermined manner as the fluid passes through the treatment device.

Figure 2:
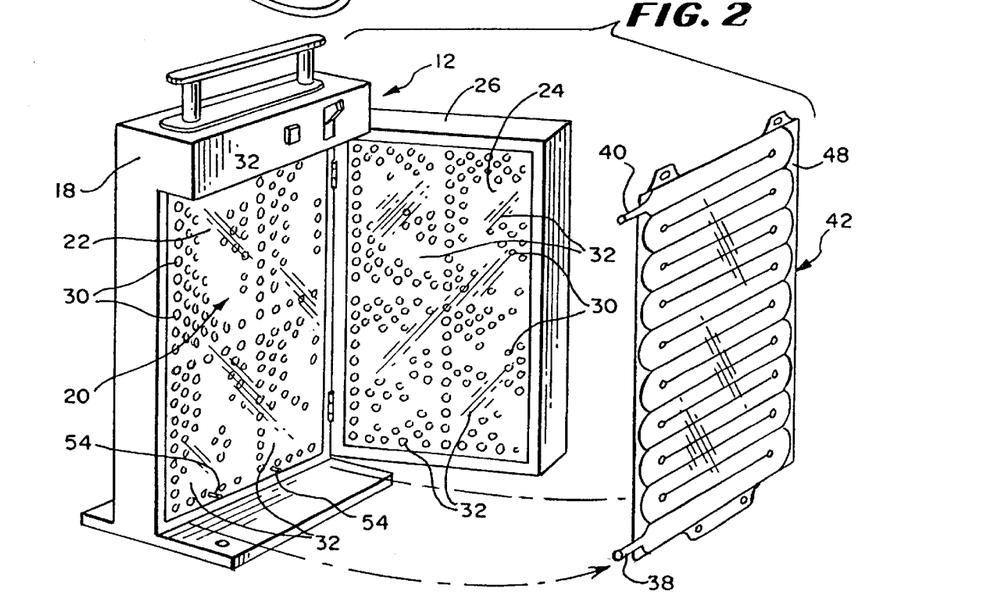
FIG. 2 is a perspective view of the system shown in FIG. 1, with the treatment chamber opened to receive the irradiation section of the associated fluid flow path prior to use.
Figure 3:
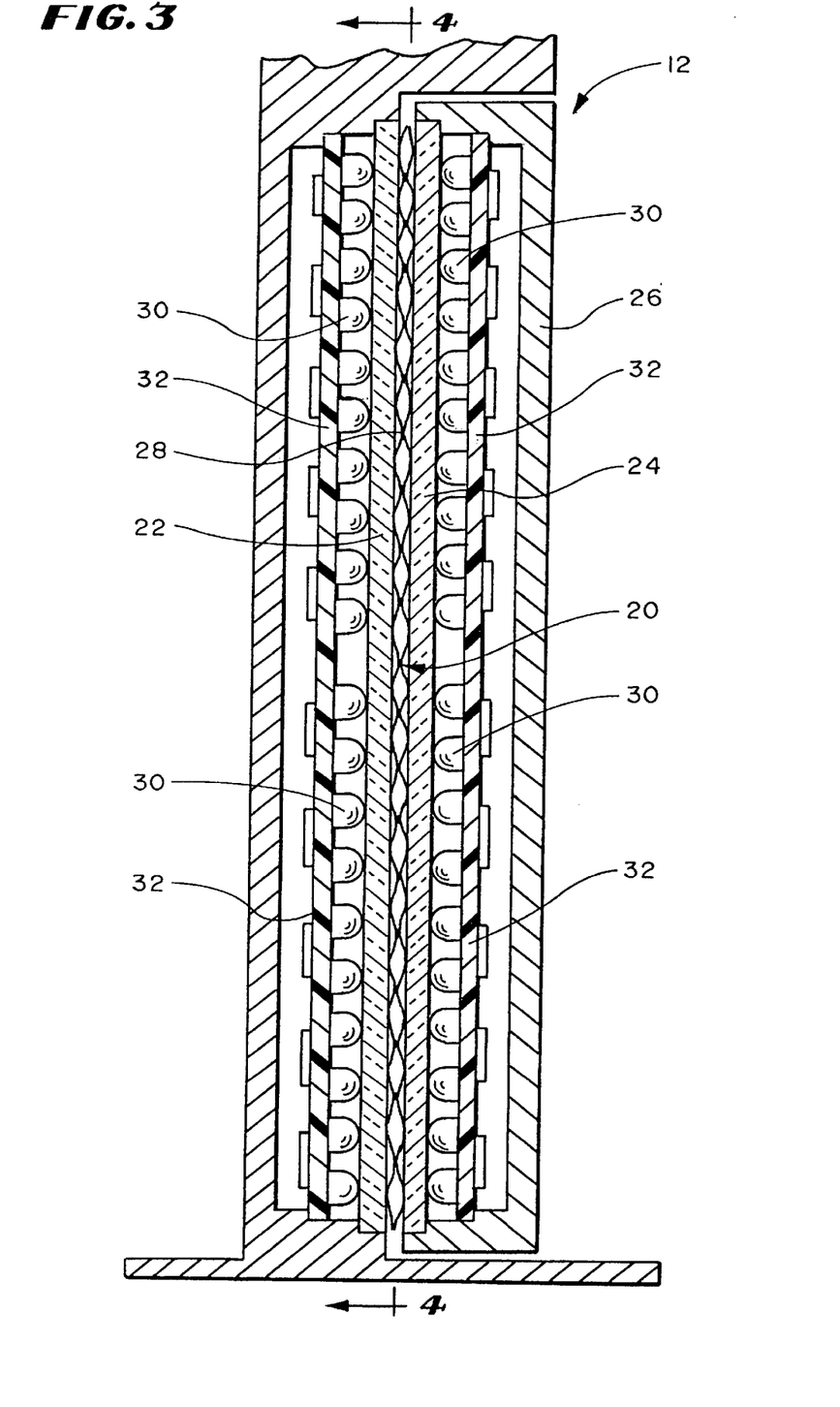
FIG. 3 is a section view of the closed treatment chamber taken generally along line 3—3 in FIG. 1.

As FIGS. 2 and 3 best show, the treatment device 12 includes body 18 that defines a treatment chamber 20. Two platens 22 and 24 on the body 18 form the treatment chamber 20. The first platen 22 is attached on the mid-portion of the body 18. The second platen 24 is carried on a door 26 that moves on the body 18 between an opened position (as FIG. 2 shows) and a closed position (as FIGS. 1 and 3 show).

As best shown in FIG. 3, when the door 26 is in its closed position, the first and second platens 22 and 24 face each other in a spaced apart relationship, thereby forming the confines of the treatment chamber 20. The space between the two platens 22 and 24 forms a gap 28 of a predetermined size through which fluid traverses the chamber 20. In the illustrated embodiment, the gap 28 is about 0.125 inch in width.

The treatment device 12 further includes a plurality of radiation sources (generally designated by the numeral 30)

positioned along the gap 28. Fluid traversing the chamber 20 is thereby exposed to the radiation sources 30. In the illustrated embodiment, each platen 22 and 24 carries a number of radiation sources 30.

According to the invention, each radiation source 30 is "discrete," meaning that each source 30 is a self-contained emitter of radiation that establishes its own zone of radiation. Being discrete, each source 30 also is capable of operation to emit a radiation independent of the emission of radiation by the other sources 30.

In the illustrated and preferred embodiment, each radiation source 30 takes the form of a photodiode. Various types of photodiodes can be selected, depending upon the fluid to be treated and the characteristics of the photoactive material used. In the illustrated embodiment, where the treated fluid contains red blood cells, all the photodiodes use transparent substrate aluminum gallium arsenide material (TS AlGaAs). Photodiodes of this type are commercially available from Hewlett-Packard Co. (Product Designation "HLMP-8150 15 Candella").

These photodiodes emit a band of radiation at a relatively narrow viewing angle of about 4 degrees. The prescribed band of radiation has a relatively precise wavelength displaying a red color having a peak wavelength of about 690 nm. Red blood cells are essentially transparent to radiation at this wavelength. The BPD's, however, are not. The BPD's absorb radiation in this wavelength to become activated.

If the fluid to be treated contains platelets, the photodiode would be selected to have a wavelength displaying a blue color having peak wavelength of about 425 nm. Platelets are essentially transparent to radiation at this wavelength.

In the illustrated embodiment, each discrete photodiode radiation source has a minimum intensity of about 8.0 cd (at 20 mA), a maximum intensity of about 36.0 cd (at 20 mA), and a typical intensity of about 15.0 cd (at 20 mA). Each photodiode operates at a low maximum forward voltage of about 2.4 V.

Figure 4:
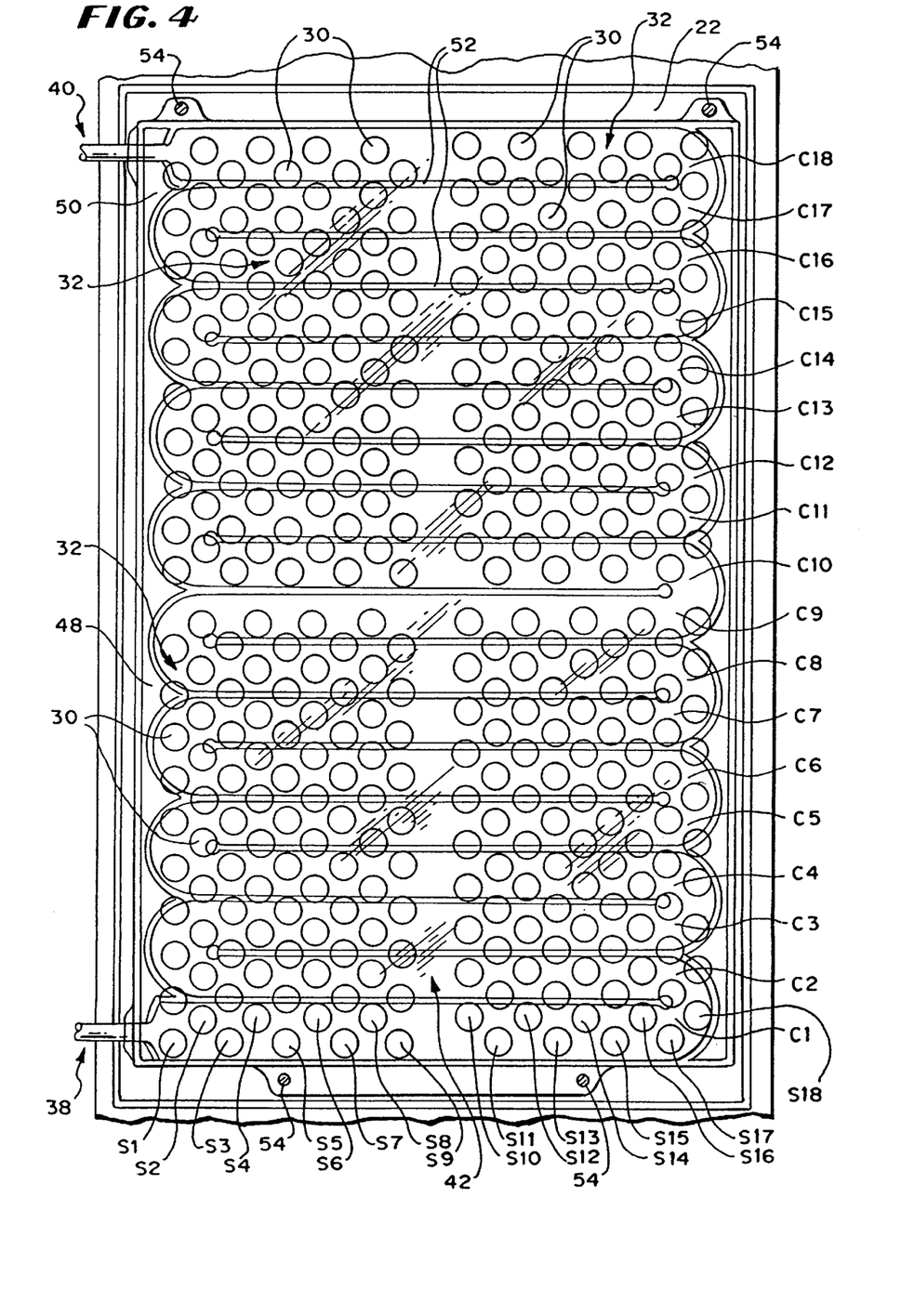
FIG. 4 is a view of the irradiation section of the fluid path in place within the treatment chamber, taken generally along line 4—4 in FIG. 3.

In the illustrated embodiment (as FIG. 4 best shows), the discrete radiation sources 30 are arranged in banks or arrays 32 on each platen 22 and 24. As FIG. 4 shows, each bank or array 32 includes a plurality of discrete sources 30 arranged in alternating rows of four and five each (shown horizontally in FIG. 4). The alternating number in each row staggers the spacing of the sources 30 between adjacent rows. In the illustrated embodiment, each array 32 includes about 90 discrete radiation sources 30.

In the illustrated arrangement (as FIG. 2 shows), four arrays 32 are carried on the body 18 behind the first platen 22 (comprising about 360 discrete sources of radiation). Four additional arrays 32 are carried on the door 26 behind the second platen 24. Each platen 22 and 24 is made of a clear glass or plastic material that is transparent to the radiation emitted by the sources.

In an alternative arrangement (not shown), only one platen 22 or 24 would carry the radiation sources 30. In this arrangement, the other platen would preferably carry a surface that reflects the radiation emitted by the sources 30 back into the gap 28. For example, the surface of the other platen could be plated with gold or like highly reflective material to reflect the wavelengths of radiation described above.

Figure 5:
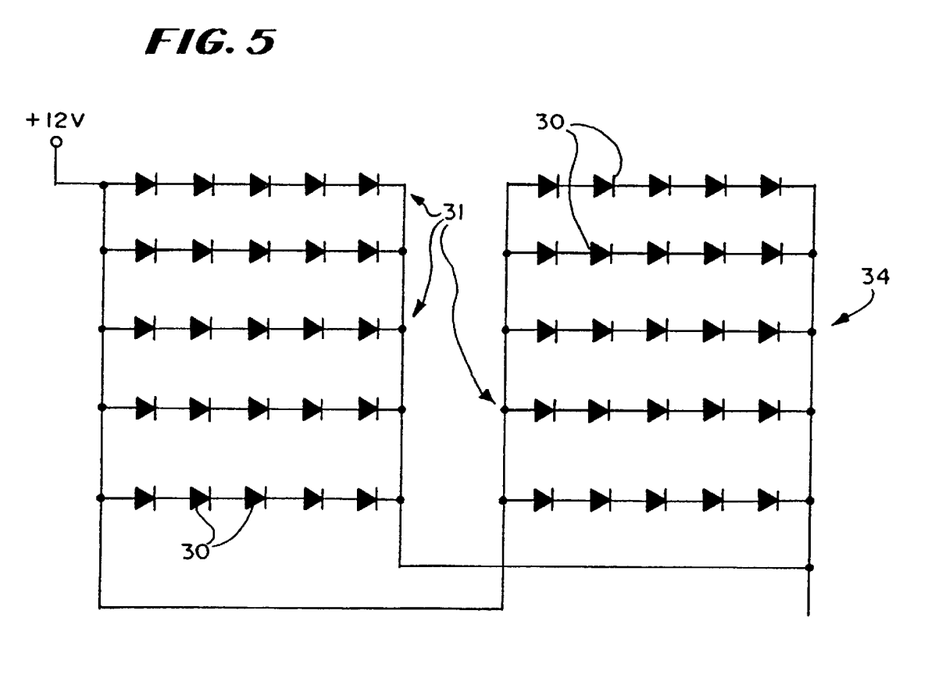
FIG. 5 is a schematic view of the control element that operates the discrete sources of radiation located within the treatment chamber.

The treatment device includes a control element 34 for operating each discrete radiation source 30 (see FIG. 5). As FIG. 5 shows, the radiation sources 30 are electrically interconnected in parallel banks 31, with each bank 31 containing five sources 30 in series connection.

As FIG. 1 shows, the fluid passes through the treatment chamber 20 from the source container 14 to the collection container 16 following a predetermined flow path 36 that embodies the features of the invention. The flow path 36 includes an inlet section 38 that conveys fluid from the source container 14 into the treatment chamber 20. The flow path 36 also includes an outlet section 40 that conveys fluid from the treatment chamber 20 to the collection container 16.

The flow path 36 further includes an intermediate irradiation section 42. One end of the irradiation section 42 communicates with the inlet section 38. Another end of the irradiation section 42 communicates with the outlet section 40.

In use (as FIG. 1 shows), the inlet and outlet sections 38 and 40 are located outside the treatment chamber 20, while the irradiation section 42 is located within the treatment chamber 20, sandwiched between the two platens. The maximum size of the flow path 36 through the irradiation section 42 is defined by the gap 28 formed between the two platens 22 and 24.

The irradiation section 42 is made of a material that is transparent to the radiation emitted by the sources. Fluid passing through the irradiation section 42 is thereby exposed to radiation.

According to the invention, the irradiation section 42 defines at least two channels (generally designated by the letter C in FIG. 4). The channels direct fluid in different successive paths past the radiation sources. In the illustrated embodiment, the irradiation section 42 includes eighteen (18) successive channels, which are numbered C1 to C18 accordingly. As FIG. 4 shows, the channels C1 to C18 are aligned in a prescribed fashion relative to the radiation sources 30 to achieve the benefits of the invention.

More particularly, the channels C1 to C18 are aligned with respect to the radiation sources 30 so that, as the fluid passes through each channel, it is exposed to at least two discrete radiation sources 30. In the illustrated embodiment, the fluid is exposed to at least eighteen discrete sources of radiation as it traverses each channel. For illustration purposes, the sources 30 associated with the first channel C1 are numbered S1 to S18 in FIG. 4.

The channels C1 to C18 are further aligned so that, as the fluid passes through the next successive channel, it is exposed to different discrete sources of radiation. For example, the eighteen radiation sources S1 to S18 in the first channel C1 are different than the radiation sources 30 associated with the next successive channel C2. In addition, there may be some overlap between sources 30 between adjacent channels.

Therefore, according to the invention, as the fluid passes through the irradiation section 42, it is not repeatedly exposed to the same source of radiation. Instead, it is exposed to numerous different sources of radiation, each one discrete unto itself. In the illustrated embodiment, the fluid is ultimately exposed at least once to about 360 discrete sources of radiation as it traverses the irradiation section 42.

In the illustrated embodiment, the source container 14, the collection container 16, and the irradiation section 42 each takes the form of a bag (respectively 44, 46, and 48) made of a flexible inert plastic material, like plasticized medical grade polyvinyl chloride. Each bag 44, 46, and 48 has heat sealed peripheral edges 50 to form a sealed interior area.

The irradiation section bag 48 further includes a series of interior heat sealed regions 52 that divide the interior area into the eighteen interconnected flow passages. The flow passage comprise the channels C1 to C18, as just described.

The irradiation section bag 48 is attached by pins 54 (see FIGS. 2 and 4) to the first platen 22. With the door 26 closed, the channels C1 to C18 formed in the bag 48 direct fluid back and forth in a serpentine path past the radiation sources 30. As before described, the fluid is exposed to several discrete radiation sources 30 in each channel of this serpentine path. And, as also before described, in each successive channel, the fluid is further exposed to several more discrete radiation sources different than those encountered in the previous channel.

In the illustrated embodiment (see FIG. 6), the inlet section 38 of the flow path 36 includes a length of flexible inert plastic tubing 56 that joins the inlet end of the irradiation section bag 48. The tubing 56 includes a conventional inline filter 58 for removing the white blood cells from the fluid prior to entering the treatment chamber 20. The filtration medium used (not shown) can include cotton wool, cellulose acetate, or another synthetic fiber like polyester.

Figure 6:
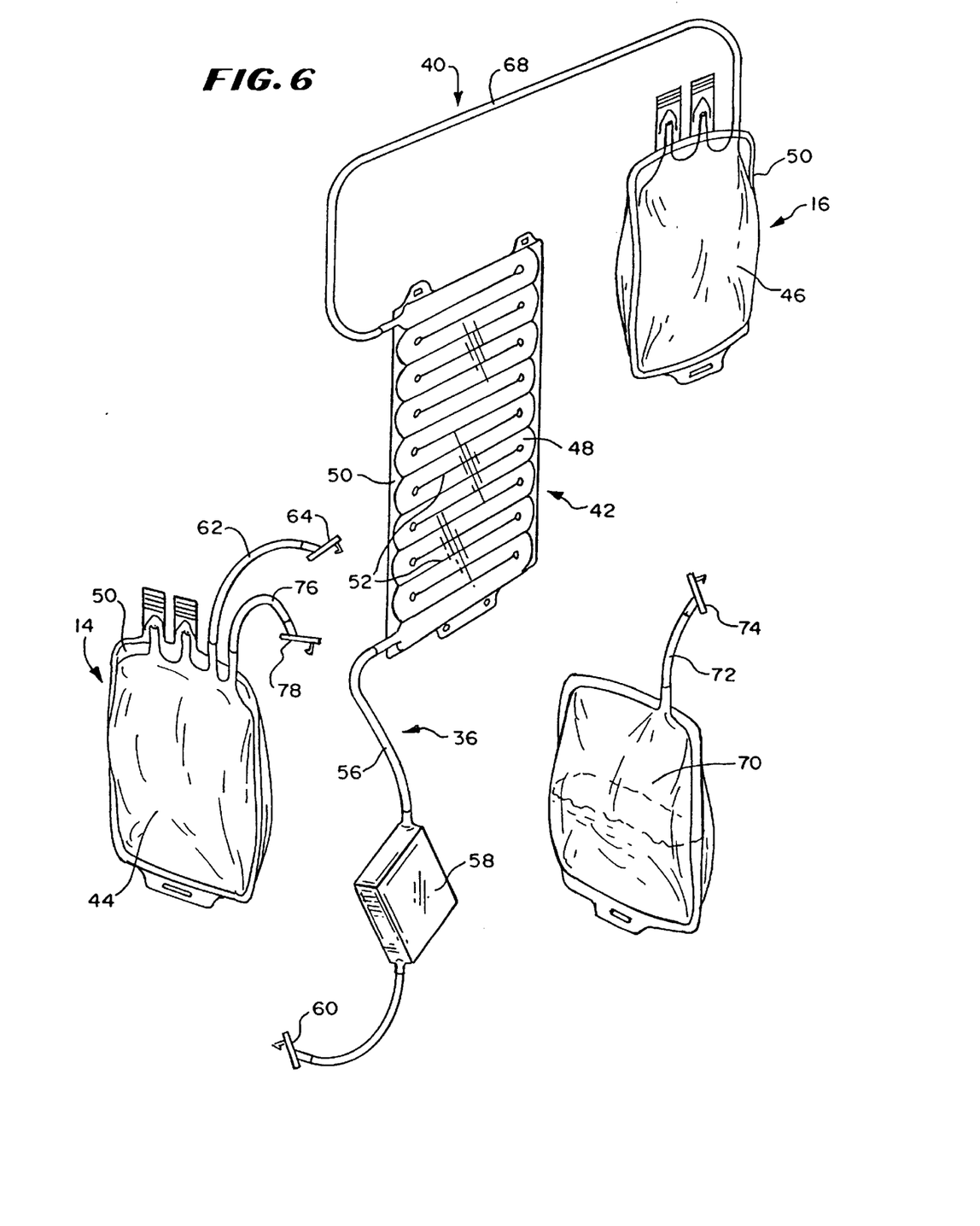
FIG. 6 is a perspective view of the component parts of the fluid flow path associated with the system shown in FIG. 1, with the component parts disassembled prior to use.

The tubing 58 terminates in a first connection device 60.

The inlet section 38 further includes a length of flexible inert plastic tubing 62 that joins the source container 14. This tubing 62 includes a second connection device 64 that mates with the first connection device 60 to join the source container 14 to the inlet end of the irradiation section bag 48.

While various known connection devices may be used, in the illustrated embodiment, the devices 60 and 64 are preferable sterile connection devices like those shown in Granzow et al U.S. Pat. Nos. 4,157,723 and 4,265,280, which are incorporated herein by reference.

In use, a peristaltic pump 66 (see FIG. 1) conveys fluid through the fluid path 36 at a predetermined flow rate. The flow rate of the pump 66 will of course vary according to the volume of fluid that is to be treated and the time limitations imposed. In the context of illustrated embodiment, it is desirable to be able to treat 300 ml of blood components in about 30 minutes. Therefore, a preferred flow rate is about 10 ml/min.

The outlet section 40 of the flow path 36 includes a length of flexible inert plastic tubing 68 that joins the outlet end of the irradiation section bag 48. The other end of the tubing 68 joins the collection container 16. In an alternative arrangement (not shown), the tubing could be normally separated into two lengths, like tubings 56 and 62, each having a (preferably sterile) connection device to join the collection container 16 to the outlet end of the irradiation section 42 prior to use.

In the illustrated embodiment (see FIG. 6), an auxiliary container 70 holds a solution containing the photoactive material. The auxiliary container 70 also includes a length of tubing 72 that carries with a third (preferably sterile) connection device 74. In this arrangement, the source container 14 also includes another length of tubing 76 that carries a fourth (preferably sterile) connection device 78. By joining the third and fourth connection devices 74 and 78, the photoactive material can be conveyed from the auxiliary container 70 into the source container 14 for mixing with the fluid to be treated. The joined tubings 72 and 76 form a closed, internally sterile path for introducing the photoactive materially into the source container 14. Once the photoactive material has been transferred, the tubing 76 can be heat sealed closed upstream of the joined connection devices 74 and 78 (as FIG. 1 shows), and the auxiliary container 70 (with joined connection devices 74 and 78) removed.

By using the sterile connection devices 60, 64, 74, and 78, the formed flow path 36 comprises a closed, internally sterile path for conveying fluid from the source container 14, through the treatment chamber 20, and into the collection container 16.

In the treatment chamber 20, the fluid is exposed to a plurality of discrete sources 30 of radiation in the manner previously described. Each discrete radiation source 30 is operated by the control element 34 at a selected wavelength within the prescribed range to activate the photoactive material bound to the contaminant as the fluid flows in succession through the channels C1 to C18 in the irradiation section 42. The photoactive material is activated by exposure to the radiation to eradicate the contaminant. The fluid containing the eradicated contaminant is collected in the container 16 for storage and subsequent transfusion.

The system 10 provides great flexibility in treating the fluid. Because each radiation source 30 is discrete, the control element 34 can be configured to operate two or more of the radiation sources at a different wavelength. Alternatively, the control element 34 can be configured to operate two or more of the discrete sources 30 of radiation at substantially the same wavelength.

Furthermore, the zone of radiation emitted by each discrete source 30 can be varied, as can the intensity of radiation of each source 30.

In the illustrated embodiment, where each platen 22 and 24 carries a number of radiation sources, the discrete sources 30 of radiation are positioned along opposite sides of the gap 28 through which the fluid flows.

Figure 7:
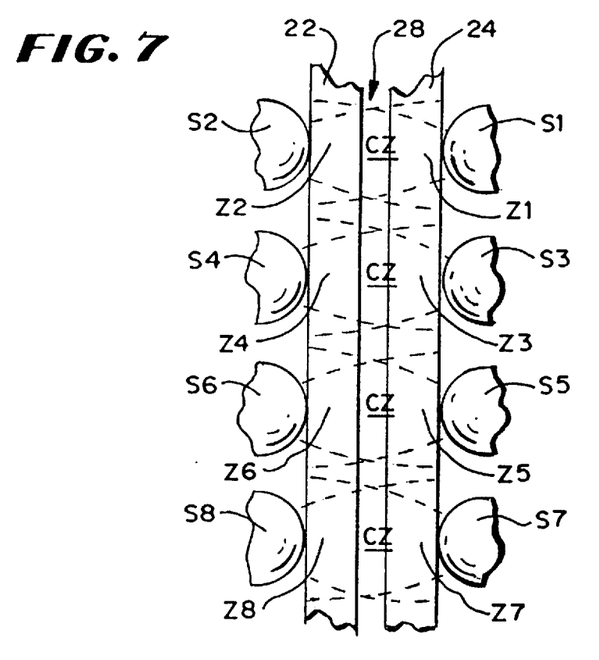
FIG. 7 is an enlarged view of a portion of the treatment chamber showing one arrangement of the discrete radiation sources along the irradiation section of the flow path.

As FIG. 7 shows, the radiation sources 30 on the platens 22 and 24 can be arranged to be diametrically opposite to each other. FIG. 7 shows four pairs of diametrically opposite sources, designated S1 to S8. In this arrangement, the zones of radiation (designated Z1 to Z8, corresponding with their sources S1 to S8) emitted by the diametrically opposite sources S1 to S8 directly overlap. The amount of radiation present in the converged zone CZ between each source is thereby intensified.

Figure 8:
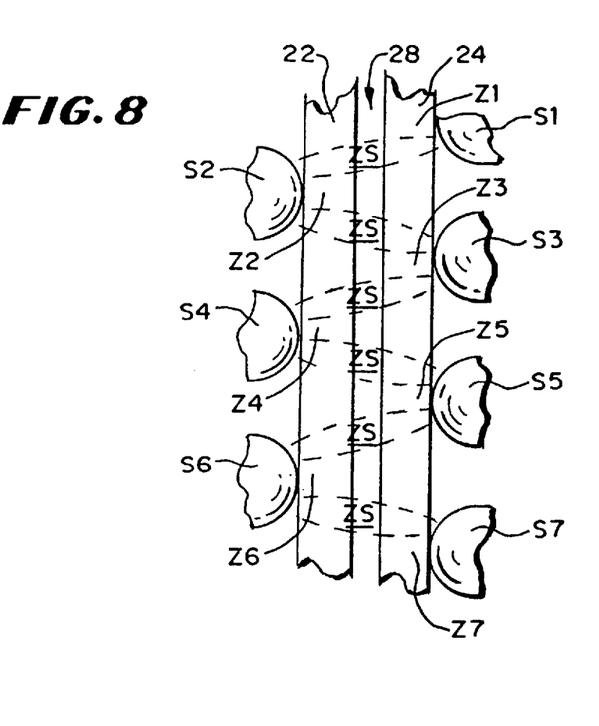
FIG. 8 is an enlarged view of a portion of the treatment chamber showing another arrangement of the discrete radiation sources along the irradiation section of the flow path.

FIG. 8 shows an alterative arrangement. In this arrangement, the radiation sources S1 to S6 on the platens do not directly face one other. Instead, the sources S1 to S6 are staggered. In this arrangement, the zones of radiation Z1 to Z6 emitted by the staggered sources do not directly overlap. Instead, they provide overlapping side regions ZS of intensified radiation between each discrete source S1 to S6.

The following example demonstrates the effectiveness of the system 10 that embodies the features of the invention to process fluid undergoing photoactive therapy at relatively high flow rates.

EXAMPLE

Human red blood cell concentrates (at a hematocrit of about 55%) containing HSV-I virus were treated in accordance with the invention. Before, treatment, BPD was added at a concentration of 4 $\mu$g/ml. The red blood cell concentrate with the BPD added was pumped through a multi-channel treatment chamber at a flow rate of 5 ml/min. The treatment chamber was radiated from each side by a bank of 360 LED's at a wavelength of about 690 nm. The viral load was reduced during the treatment by two orders of magnitude (99%) from $10^6$ units/ml to $10^4$ units/ml.

The features and advantages of the invention are set forth in the following claims.

We claim:

1. A system for treating a fluid carrying a contaminant to which a photoactive material has been bound, the material being activated by exposure to radiation within a prescribed wavelength range to eradicate the contaminant, the system comprising a first platen and a second platen forming a treatment area between them, means for moving the first platen with respect to the second platen to open and close the treatment area, at least one of the first and second platens comprising a surface that is transparent to radiation within the prescribed wavelength range, an array of photodiodes mounted behind the transparent surface of the one platen, the photodiodes each comprising a discrete source of radiation, a chamber having opposed side walls, at least one of which is transparent to radiation within the prescribed wavelength range, the chamber including an inlet for receiving the fluid to be treated, an outlet for discharging the fluid, and a flow channel for conveying the fluid between the inlet and outlet ends along a predetermined path within the chamber, means accessible when the treatment area is opened for mounting the chamber in the treatment area with the transparent side wall of the chamber facing the transparent surface of the one platen and for thereafter holding the chamber between the platens when the treatment area is closed, and means for operating each photodiode at a selected wavelength within the prescribed range to activate the photoactive material bound to the contaminant during passage of the fluid through the flow channel.

2. A system according to claim 1 wherein at least two of the photodiodes in the array are operated at different wavelengths.

3. A system according to claim 1 wherein at least two of the photodiodes in the array are operated at substantially the same wavelength.

4. A system according to claim 1 wherein at least two of the photodiodes in the array are operated at different intensities.

5. A system according to claim 1 wherein at least two of the photodiodes in the array are operated at substantially the same intensity.

6. A system according to claim 1 wherein both the first and second platens comprise a surface that is transparent to radiation within the prescribed wavelength range, wherein an array of photodiodes is carried behind the transparent surfaces of both platens, the photodiodes each comprising a discrete source of radiation.

7. A system according to claim 6 wherein both side walls of the chamber are transparent to radiation within the prescribed wavelength range.

8. A system according to claim 1 wherein the other one of the platens includes a surface that reflects radiation within the prescribed wavelength range.

9. A system according to claim 8 wherein both side walls of the chamber are transparent to radiation within the prescribed wavelength range.

10. A system according to claim 1 wherein the means for moving the first platen with respect to the second platen comprises hinge means for moving the first platen as a door between an opened position and a closed position with respect to the second platen.

11. A blood collection assembly comprising a blood source container having a first inlet port for receiving blood, a second inlet port, and an outlet port, a second source container holding a photoactive material that binds to a contaminant within blood, the photoactive material being activated by exposure to radiation within a prescribed wavelength range to eradicate the contaminant, the second source container having an outlet port connectable to the second inlet port of the blood source container for conveying the photoactive material into the blood source container, a blood collection container having an inlet port, a treatment chamber having an inlet port integrally joined by tubing to the outlet port of the blood source container and an outlet port integrally joined by tubing to the inlet port of the blood collection chamber, the treatment chamber including means defining a channel for conveying blood between the inlet and outlet ports of the treatment chamber, the treatment chamber having at least one wall portion overlying the channel that is made of a material that is transparent to radiation within the prescribed wavelength range, a first platen and a second platen forming a treatment area between them, means for moving the first platen with respect to the second platen to open and close the treatment area, at least one of the first and second platens comprising a surface that is transparent to radiation within the prescribed wavelength range, an array of photodiodes mounted behind the transparent surface o the one platen, the photodiodes each comprising a discrete source of radiation, means accessible when the treatment area is opened for mounting the treatment chamber in the treatment area with the transparent portion of the treatment chamber facing the transparent surface of the one platen and for thereafter holding the treatment chamber between the platens when the treatment area is closed, and means for operating each photodiode at a selected wavelength within the prescribed range to activate the photoactive material bound to the contaminant during passage of the fluid through the treatment chamber channel.

12. A method for collecting blood essentially free of an undesired contaminant comprising the steps of conveying the blood into a source container that contains a photoactive material that binds to the contaminant, the material being activated by exposure to radiation within a prescribed wavelength range to eradicate the contaminant, conveying the blood and photoactive material from the source into a treatment chamber, exposing the blood within the treatment chamber to an array of discrete sources of radiation comprising photodiodes while operating the photodiodes at a selected wavelength within the prescribed range to activate the photoactive material bound to the contaminant, the blood being conveyed along a flow path in which it is successively exposed to several photodiodes located along the flow path, each photodiode comprising a discrete source of radiation that is operated at a selected wavelength within the prescribed range, and conveying the blood from the treatment container to a collection container.

13. A method according to claim 12 and further including the step of filtering white blood cells from the blood before conveying it into the treatment chamber.

14. A method according to claim 12 wherein, in the step of operating the sources of radiation, at least two of the photodiodes are operated at different wavelengths.

15. A method according to claim 12 wherein, in the step of operating the sources of radiation, at least two of the photodiodes are operated at substantially the same wavelength.

16. A method according to claim 12 wherein, in the step of operating the sources of radiation, at least two of the photodiodes are operated at different intensities.

17. A method according to claim 12 wherein, in the step of operating the sources of radiation, at least two of the photodiodes are operated at substantially the same intensity.

18. A method according to claim 12 wherein, into the treatment chamber, and into the collection container, the blood is conveyed through internally sterile paths closed from communication with the atmosphere.

* * * * *